(12) United States Patent
Kamiyama

(10) Patent No.: US 9,138,202 B2
(45) Date of Patent: Sep. 22, 2015

(54) ULTRASONIC DIAGNOSIS APPARATUS AND MEDICAL IMAGE PROCESSING METHOD

(75) Inventor: Naohisa Kamiyama, Otawara (JP)

(73) Assignees: KABUSHIKI KAISHA TOSHIBA, Tokyo (JP); Toshiba Medical Systems Corporation, Otawara-shi (JP)

(*) Notice: Subject to any disclaimer, the term of this patent is extended or adjusted under 35 U.S.C. 154(b) by 773 days.

(21) Appl. No.: 12/790,080

(22) Filed: May 28, 2010

(65) Prior Publication Data

US 2010/0312112 A1     Dec. 9, 2010

(30) Foreign Application Priority Data

Jun. 9, 2009   (JP) ................. 2009-138569

(51) Int. Cl.
  *A61B 8/00*     (2006.01)
  *A61B 8/14*     (2006.01)
  *G06T 7/00*     (2006.01)
  *A61B 8/08*     (2006.01)

(52) U.S. Cl.
  CPC ............... *A61B 8/14* (2013.01); *G06T 7/0065* (2013.01); *G06T 7/0083* (2013.01); *A61B 8/483* (2013.01); *G06T 2207/10136* (2013.01); *G06T 2207/30056* (2013.01)

(58) Field of Classification Search
  None
  See application file for complete search history.

(56) References Cited

U.S. PATENT DOCUMENTS

| | | | |
|---|---|---|---|
| 2004/0144176 A1* | 7/2004 | Yoden | 73/628 |
| 2004/0252870 A1 | 12/2004 | Reeves et al. | |
| 2005/0240104 A1* | 10/2005 | Shim et al. | 600/437 |
| 2006/0253029 A1* | 11/2006 | Altmann et al. | 600/466 |
| 2007/0282543 A1* | 12/2007 | Hiyama et al. | 702/39 |
| 2008/0069445 A1* | 3/2008 | Weber | 382/181 |

(Continued)

FOREIGN PATENT DOCUMENTS

| | | |
|---|---|---|
| EP | 1 832 233 A1 | 9/2007 |
| JP | 54-99380 | 8/1979 |

(Continued)

OTHER PUBLICATIONS

Extended European Search Report dated Oct. 6, 2010 in corresponding European Application No. 10 00 5914.

(Continued)

*Primary Examiner* — Unsu Jung
*Assistant Examiner* — Michael N Fisher
(74) *Attorney, Agent, or Firm* — Oblon, McClelland, Maier & Neustadt, L.L.P.

(57) ABSTRACT

According to one embodiment, an ultrasonic diagnosis apparatus includes an ultrasonic probe, an ultrasonic transmission/reception unit which generates echo signals associated with scan planes by transmitting and receiving ultrasonic waves to and from an object via the ultrasonic probe, an image data generating unit which generate tomogram data respectively corresponding to the scan planes based on the echo signals, a contour line extraction processing unit which extracts contour lines of a specific region from the plurality of tomograms, a contour line processing unit which generates curves respectively corresponding to the extracted contour lines, and a surface image generating unit which generates one-dimensional brightness trains on the curves from the tomograms and generates a surface image expressing the surface unevenness of the specific region with brightness changes by arraying the brightness trains in accordance with the positions of the corresponding scan planes.

11 Claims, 7 Drawing Sheets

(56) References Cited

U.S. PATENT DOCUMENTS

| | | | |
|---|---|---|---|
| 2008/0146929 A1* | 6/2008 | Satoh | 600/443 |
| 2008/0317308 A1* | 12/2008 | Wu et al. | 382/128 |
| 2009/0030314 A1* | 1/2009 | Kawae | 600/443 |
| 2009/0097722 A1* | 4/2009 | Dekel et al. | 382/128 |

FOREIGN PATENT DOCUMENTS

| | | |
|---|---|---|
| JP | 56-13936 | 2/1981 |
| JP | 57-37441 | 3/1982 |
| JP | 64-64631 | 3/1989 |
| JP | 4-307042 | 10/1992 |
| JP | 8-38475 | 2/1996 |
| JP | 3050374 | 3/2000 |
| JP | 2003-61964 | 3/2003 |
| JP | 2003-514600 | 4/2003 |
| JP | 2005-523053 | 8/2005 |
| JP | 2008-142448 | 6/2008 |
| JP | 2008-272087 | 11/2008 |
| WO | WO 01/80185 A1 | 10/2001 |
| WO | WO 2006/068271 | 6/2006 |

OTHER PUBLICATIONS

Office Action mailed Aug. 6, 2013, in Japanese Patent Application No. 2009-138569 (with English-language Translation).

* cited by examiner

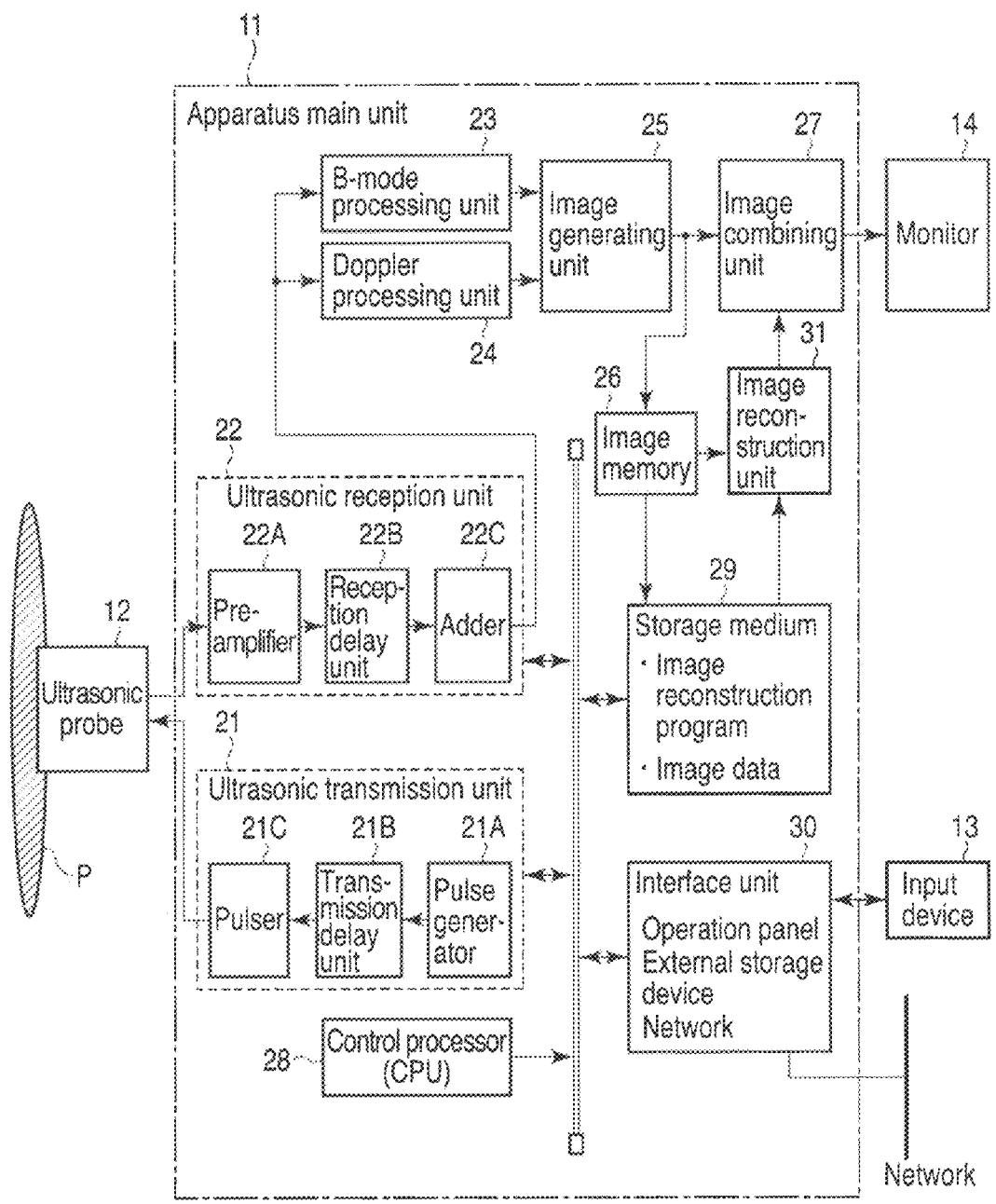
F I G. 1

ULTRASONIC DIAGNOSIS APPARATUS AND MEDICAL IMAGE PROCESSING METHOD

CROSS-REFERENCE TO RELATED APPLICATIONS

This application is based upon and claims the benefit of priority from Japanese Patent Application No. 2009-138569, filed Jun. 9, 2009; the entire contents of which are incorporated herein by reference.

FIELD

Embodiments described herein relate generally to an ultrasonic diagnosis apparatus and a medical image processing apparatus.

BACKGROUND

An ultrasonic diagnosis apparatus is a diagnosis apparatus to display images of in vivo information. The ultrasonic diagnosis apparatus is used as a useful apparatus for noninvasive observation in real time at low cost without exposure to radiation as compared with other image diagnosis apparatuses such as an X-ray diagnosis apparatus and an X-ray computed tomography apparatus. The ultrasonic diagnosis apparatus has a wide range of applications including diagnosis of circulatory organs such as the heart, abdominal organs such as the liver and kidney, and peripheral vessels, diagnosis in obstetrics and gynecology, and diagnosis of breast cancer.

In general, the ultrasonic diagnosis apparatus obtains one-dimensional vital information by a one-time pulse transmitted from a probe. Repeatedly performing such transmission/reception while changing the transmitting direction can reconstruct a two-dimensional tomogram. This image represents the form of an organ or the like in an object and is called a B-mode image or simply called a tomogram, which is a most basic picture mode for ultrasonic diagnosis.

Likewise, repeatedly performing transmission/reception in three-dimensional directions can obtain three-dimensional information of a living body organ. Currently, visualization of three-dimensional information using ultrasonic waves has already been clinically used owing to a technique of three-dimensionally changing the transmitting/receiving direction by mechanically swinging the probe or electronically controlling the delays of a plurality of transducers two-dimensionally arrayed.

Using three-dimensional information can perform image reconstruction which cannot be performed by using a simple tomogram like a conventional B-mode image. This makes it possible to improve the efficiency of diagnosis and provide new diagnosis information. For fetal observation, for example, tomographic observation of a fetus is the mainstream technique in the normal B mode. In contrast, using three-dimensional information makes it possible to reconstruct an image of the face of a fetus such that the surface of the face looks as if it were imaged by a camera.

It is not always possible to implement a three-dimensional image like that described in the case of the fetus in all cases. In the case of a fetus, amniotic fluid exists between the surface of the fetus and the probe. The amniotic fluid generally includes no ultrasonic echo, and hence the surface of an object of interest can be imaged relatively easily. This applies to the inner walls of the heart, blood vessels, and bile ducts. Since a blood portion in a cardiac chamber or the like includes no echo, it is easy to visualize the surface of the blood portion.

In other cases, however, it is not easy to observe surfaces with ultrasonic waves. Assume that the state of the surface of a tumor in the liver is to be imaged. In this case, solid echo signals also exist outside the tumor. For this reason, in order to observe the surface of the tumor, it is necessary to carefully remove signals outside the tumor.

The observation of the surface of the liver has attracted attention. In some cases, the tissue properties of the liver diffusedly change from the onset of hepatitis up to hepatic cirrhosis. However, a characteristic of hepatitis also appears on the liver surface. That is, the surface becomes uneven. Currently, such a state is optically observed with an abdominal endoscope. This technique is to observe the surface of an abdominal region of a patient by inserting an endoscope (camera) into a small hole formed in the abdominal region of the patient under anesthesia. Since an air gap is generally provided between the liver and the peritoneum, such optical observation can be done.

If, however, an image of the liver surface like that described above is to be obtained by an ultrasonic diagnosis apparatus, since the liver surface is in contact with the peritoneum, it is difficult to image the liver surface by using general three-dimensional ultrasonic waves as in the case of the tumor surface described above.

BRIEF DESCRIPTION OF THE DRAWINGS

FIG. 1 is a block diagram showing the arrangement of an ultrasonic diagnosis apparatus according to an embodiment;

DETAILED DESCRIPTION

Figure 2:
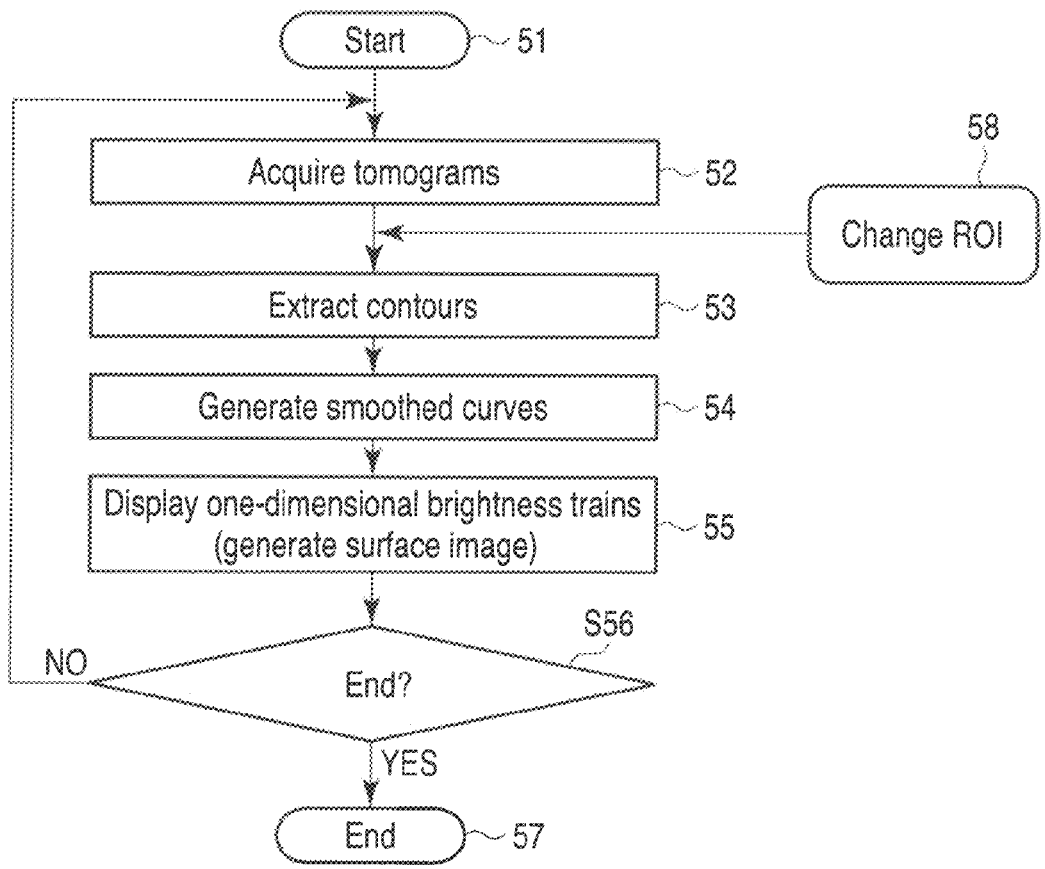
FIG. 2 is a flowchart showing a surface image generating procedure according to this embodiment.

In general, according to one embodiment, an ultrasonic diagnosis apparatus includes an ultrasonic probe, an ultrasonic transmission/reception unit which generates echo signals associated with a plurality of scan planes by transmitting and receiving ultrasonic waves to and from an object via the ultrasonic probe, an image data generating unit which generate a plurality of tomogram data respectively corresponding to the plurality of scan planes based on the echo signals, a contour line extraction processing unit which extracts a plurality of contour lines of a specific region from the plurality of tomograms, a contour line processing unit which generates a plurality of curves respectively corresponding to the plurality of extracted contour lines, and a surface image generating unit which generates a plurality of one-dimensional brightness trains on the plurality of curves from the plurality of tomograms and generates a surface image expressing the surface unevenness of the specific region with brightness changes by arraying the brightness trains in accordance with the positions of the corresponding scan planes.

FIG. 1 shows the arrangement of the ultrasonic diagnosis apparatus according to this embodiment. This ultrasonic diagnosis apparatus includes an ultrasonic diagnosis apparatus main unit 11, an ultrasonic probe 12, an input device 13, and a monitor 14. The ultrasonic probe 12 includes a plurality of piezoelectric transducers which generate ultrasonic waves upon receiving driving signals from an ultrasonic reception unit 22 of the apparatus main unit 11 and convert reflected waves from an object into electrical signals, a matching layer provided for the piezoelectric transducers, and a backing member which prevents ultrasonic waves from propagating backward from the piezoelectric transducers. When the ultrasonic probe 12 transmits an ultrasonic wave to an object P, the transmitted ultrasonic wave is sequentially reflected by a discontinuity surface of acoustic impedance of body tissue, and is received as an echo signal by the ultrasonic probe 12. The amplitude of this echo signal depends on an acoustic impedance difference on the discontinuity surface by which the echo signal is reflected. The echo produced when a transmitted ultrasonic pulse is reflected by the surface of a moving blood flow, cardiac wall, or the like is subjected to a frequency shift depending on the velocity component of the moving body in the ultrasonic transmitting direction due to a Doppler effect.

The input device 13 includes various types of switches, buttons, a trackball, a mouse, and a keyboard which are used to input, to the apparatus main unit 11, various types of instructions and conditions, an instruction to set a region of interest (ROI), various types of image quality condition setting instructions, and the like from an operator. The monitor 14 displays morphological information and blood flow information in the living body as images based on video signals from an image generating unit 25.

The apparatus main unit 11 includes the ultrasonic transmission unit 21, the ultrasonic reception unit 22, a B-mode processing unit 23, a Doppler processing unit 24, the image generating unit 25, an image memory 26, an image combining unit 27, a control processor 28, a storage medium 29, an interface unit 30, and an image reconstruction unit 31. The ultrasonic transmission unit 21, the ultrasonic reception unit 22, and the like of the apparatus main unit 11 are implemented by hardware such as an integrated circuit in some cases, and are software programs in the form of software modules in other cases. The function of each constituent element will be described below.

The ultrasonic transmission unit 21 includes a pulse generator 21A, a transmission delay unit 21B, and a pulser 21C. The pulse generator 21A repetitively generates rate pulses for the formation of transmission ultrasonic waves at a predetermined rate frequency fr Hz (period: 1/fr sec). The transmission delay unit 21B gives each rate pulse a delay time necessary to focus an ultrasonic wave into a beam and determine transmission directivity for each channel. The pulse generator 21A applies a driving pulse to the probe 12 at the timing based on a rate pulse for each channel.

The ultrasonic reception unit 22 includes a preamplifier 22A, an A/D converter (not shown), a reception delay unit 22B, and an adder 22C. The preamplifier 22A amplifies an echo signal received via the probe 12 for each channel. The reception delay unit 22B gives the amplified echo signals delay times necessary to determine reception directivities. The adder 22C then performs addition processing. With this addition, the reflected component of the echo signal from the direction corresponding to the reception directivity is enhanced, and a synthetic beam for ultrasonic transmission/reception is formed in accordance with the reception directivity and the transmission directivity.

The B-mode processing unit 23 receives an echo signal from the reception unit 22, and performs logarithmic amplification, envelope detection processing, and the like for the signal to generate data expressing the intensity of the signal with brightness. The image generating unit 25 converts the output data from the B-mode processing unit 23 into a B-mode image expressing the intensity of a reflected wave with brightness by using a predetermined lookup table. The monitor 14 displays the B-mode image.

The Doppler processing unit 24 frequency-analyzes velocity information from the echo signal received from the reception unit 22, extracts a blood flow or tissue owing to a Doppler effect and a contrast medium echo component, and obtains blood information such as mean velocities, variances, powers, and the like at multiple points. The obtained blood flow information is sent to the image generating unit 25 to be converted into a mean velocity image, a variance image, a power image, or a combined image thereof, and is displayed in color on the monitor 14.

The image generating unit 25 generates an ultrasonic diagnosis image as a display image by converting the scanning line signal string for ultrasonic scanning into a scanning line signal string in a general video format typified by a TV format or the like. The image generating unit 25 includes a memory to store image data, and allows an operator to retrieve a recorded image during examination after diagnosis. Note that data before it is input to the image generating unit 25 is sometimes called "raw data".

The image memory 26 includes a memory to store the image data received from the image generating unit 25. The operator can retrieve this image data after diagnosis, and can reproduce the data as a still image or a moving image by using a plurality of frames.

The storage medium 29 stores a scan sequence (to be described later), a control program for executing image generation/display processing, diagnosis information (a patient ID, findings by a doctor, and the like), a diagnosis protocol, transmission/reception conditions, and other data. The storage medium 29 is also used to store images in the image memory 26, as needed. The storage medium 29 also stores an image processing program for generating a new image unique to this embodiment (to be described later). Data in the storage medium 29 can be transferred to an external peripheral apparatus via the interface unit 30.

The control processor 28 is a control unit which has a function as an information processing apparatus (computer) and controls the operation of this ultrasonic diagnosis apparatus main unit. The control processor 28 reads out control programs for executing image generation/display processing (to be described later) and the like, and executes computation/control and the like associated with various types of processing.

The interface unit 30 is an interface associated with the input device 13, a network, and a new external storage device (not shown). The interface unit 30 can transfer data such as ultrasonic images, analysis results, and the like obtained by this apparatus to another apparatus via the network.

The image reconstruction unit 31 is an image processing unit which receives images from the image memory 26 or image data obtained from the image memory 26 via the storage medium 29, and generates new images according to this embodiment. The generated images are sent to the image combining unit 27 and displayed on the monitor 14 in parallel with normal diagnosis images.

This embodiment generates new images by the following processing and functions in order to express the surface unevenness of a region of interest such as an organ by simple processing with high reproducibility/reliability. A new image is an image expressing the surface unevenness of a region of interest such as the liver with brightness, and will be referred to as a "surface image" hereinafter. A new "surface image" according to this embodiment essentially differs from an existing surface image generated from volume data by projection processing in terms of processing steps. An existing surface image is generated by projection processing and rendering from volume data generated from a plurality of multislice images by interpolation processing, coordinate conversion, and the like. In contrast, a new "surface image" (to be simply referred to as a surface image hereinafter) according to this embodiment can be generated by simpler processing with a considerably reduced number of processing steps, as described below. This makes it possible to similarly generate images concurrently with scanning.

This apparatus performs three-dimensional scanning. Three-dimensional scanning is implement by moving a two-dimensional scan plane during a period in which two-dimensional scanning is repeated. The apparatus moves a two-dimensional scan plane by manually moving the ultrasonic probe on the body surface of an object, or electronically or mechanically rotating a two-dimensional scan plane, or electronically or mechanically swinging a two-dimensional scan plane. Three-dimensional scanning will generate a plurality of tomograms covering an organ of interest.

For surface image generation processing, first of all, this apparatus includes a function of extracting, for each image, the contour of an organ of interest (a contour line; see reference numeral 62 in FIG. 8) from pixel value (the amplitude of a reception signal) differences of a tomogram (image tone or brightness changes of an image) by threshold processing or the like. With this operation, positions on the surface of the organ of interest are estimated. A contour line meanders in accordance with the surface unevenness of the organ of interest.

Second, the apparatus specifies a characteristic new curve (rough contour line) passing between a train of depth local maximum points on the meandering contour line and a train of depth local minimum points on the contour line. Note that the "depth" is the linear distance from the probe to a target. The "depth local maximum point" is the deepest point within a local range on the contour line. The "depth local minimum point" is the shallowest point within a local range on the contour line.

A typical example of a rough contour line is a smoothed curve (see reference numeral 63 in FIG. 8) obtained by smoothing the depth changes of the rough contour line. This makes it possible to obtain a smoothed curve passing through almost the middles of concave and convex portions of the surface of the organ of interest while crossing the rough contour line meandering in accordance with the surface unevenness.

Third, the apparatus generates a new image by using a train of pixel values or brightness values on the smoothed curve. Each brightness on the extracted contour line exhibits almost the maximum brightness value in its surrounding area. In contrast, the brightness at a position distant from the contour line decreases depending on the distance to some extent. That is, the brightness value changes on the smoothed curve reflect the surface unevenness of the organ of interest.

The technique according to this embodiment can obtain only the information of a one-dimensional brightness value train as a "new image (surface image)" obtained from one B-mode tomogram. It is however possible to generate a surface image as a new two-dimensional image by collecting a plurality of brightness value trains from a plurality of consecutive B-mode images, i.e., three-dimensional ultrasonic data, and arraying them in accordance with scanning positions. It is eventually possible to provide an examiner with this surface image as an image expressing the surface unevenness of the organ of interest with brightness levels.

When an operator simply scans, for example, the liver slowly and three-dimensionally, it is possible to visualize the state of a liver surface and allow easy diagnosis of the state of the unevenness of the liver surface.

Figure 3:
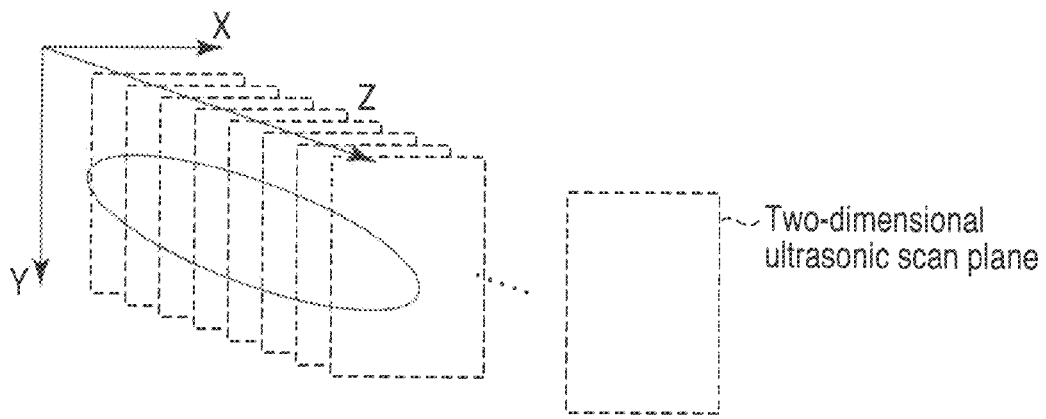
FIG. 3 is a supplementary view for step 52 in FIG. 2.
Figure 4:
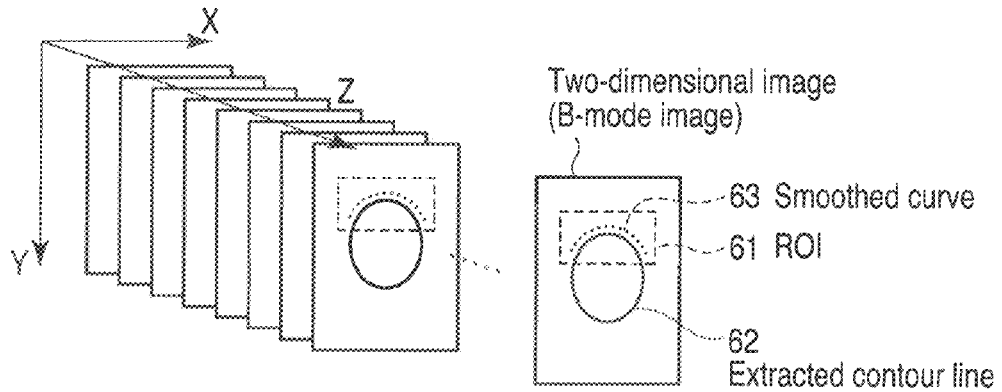
FIG. 4 is a supplementary view for steps 52 and 53 in FIG. 2.

A procedure for generating a new surface image according to this embodiment will be described in detail below. FIG. 2 shows a procedure for this processing. First of all, the operator performs input operation by using a button or the like of the input device 13 to start a surface image generation technique according to this embodiment (51). As shown in FIG. 3, slowly moving the probe 12 on, for example, a body surface corresponding to the liver will scan a three-dimensional region including the liver. Note that a two-dimensional scan plane is defined on the X- and Y-axes, and the moving direction of the two-dimensional scan plane is defined on the Z-axis. Three-dimensional scanning is arbitrary. It is possible to make the operator move the probe 12 while repeating two-dimensional ultrasonic scanning or to move the probe 12 mechanically or electronically. Performing three-dimensional scanning will generate echo signals associated with a plurality of scan planes. As shown in FIG. 4, the image generating unit 25 then generates data of a plurality of tomograms respectively corresponding to the plurality of scan planes based on the echo signals.

Figure 6:
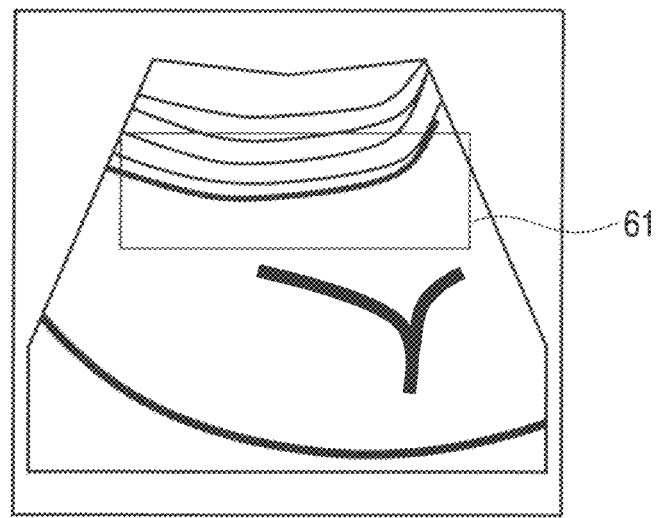
FIG. 6 is a supplementary view for step 58 in FIG. 2.

The data of a two-dimensional tomogram from the image generating unit 25 is sent to the image reconstruction unit 31 (52). The image reconstruction unit 31 then extracts the contour of an organ surface or tumorous lesion from the sent tomogram (53). At this time, the tomogram may include a plurality of organ surfaces undesired by the examiner. As shown in FIG. 6, therefore, the examiner can set a region of interest (ROI) 61 on the tomogram so as to locally limit a region from which a contour is to be extracted. The operator can arbitrarily change the size and position of the ROI 61 with the input device 13 (58). As another example of such technique, it is possible to use a means for automatically predicting a region from which a contour is to be extracted, by designating a preset for designating a diagnosis region before examination. If, for example, a "liver surface" is selected as a preset, the apparatus analyzes a near-distance region like that shown as the ROI 61 in FIG. 6.

Figure 7:
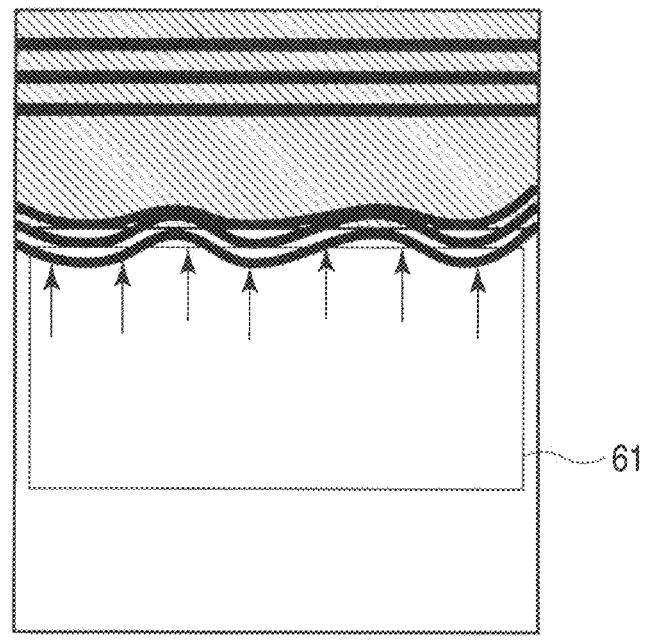
FIG. 7 is a supplementary view for step 53 in FIG. 2.

Although various methods have currently been proposed as contour extraction techniques, since an ultrasonic diagnosis image expresses an organ contour with brightness levels, it is possible to use an arbitrary proper means of contour extraction techniques using brightness values (the intensities of reception signals). FIG. 7 shows an example of this technique. In this case, the apparatus searches the set ROI 61 from a lower end to an upper portion for a maximum brightness point and eventually extracts a marginal curve extending laterally. Note that the above algorithm may use a method of substituting "a point reaching a given threshold" for a "maximum brightness point".

Figure 8:
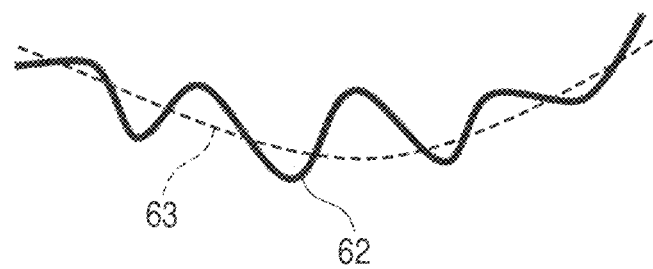
FIG. 8 is a supplementary view for step 54 in FIG. 2.

As shown in FIG. 8, the apparatus generates a "smoothed curve 63" for final imaging based on a contour line 62 after contour extraction (54). The smoothed curve 63 is a curve smoothly and approximately tracking the extracted contour line 62, and is obtained by, for example, smoothing (averaging) the coordinates of the contour line (depths) by moving average processing.

The following is a reason why the smoothed curve 63 is obtained (FIG. 8). That is, the extracted contour line 62 is obtained by extracting maximum brightnesses, and hence the brightnesses on the curve are almost equally high. In contrast, as shown FIG. 8, the smoothed curve 63 repeatedly crosses the contour line 62, and hence high and low brightnesses alternately appear on the smoothed curve 63. In addition, regarding a smooth contour, the contour line 62 and the smoothed curve 63 exhibit almost the same shape, and hence high and low brightnesses appear less frequently.

The train of brightness values on the smoothed curve obtained by the algorithm according to this embodiment has information which can express the state of the unevenness of the contour with brightness changes.

Figure 5:
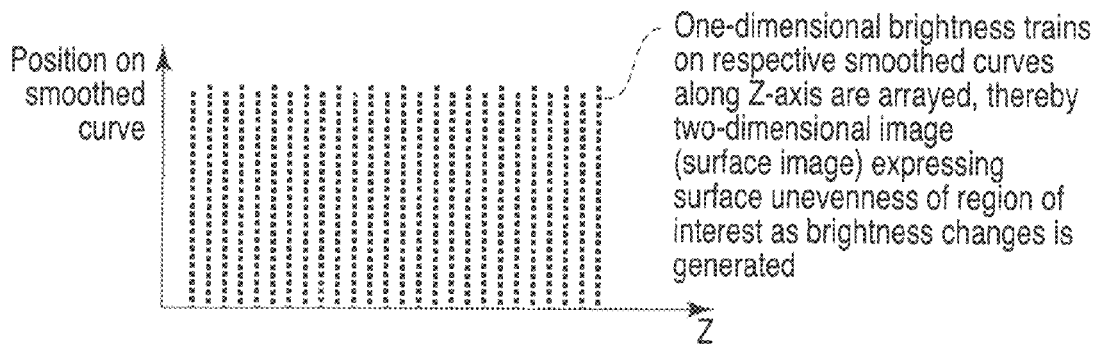
FIG. 5 is a supplementary view for step 55 in FIG. 2.
Figure 9:
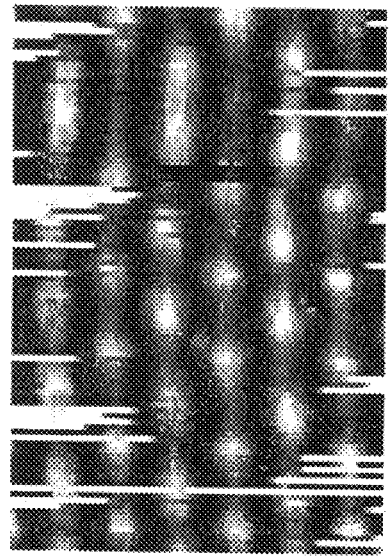
FIG. 9 is a view showing an example of the surface image obtained in step 55 in FIG. 2.

Brightness values on the smoothed curve are displayed as a new surface image (55). Note however that performing the above processing only once will obtain a one-dimensional straight line as a resultant image. Therefore, another straight line is added by performing the processing in steps 52 to 55 again for the ultrasonic tomogram obtained afterward. Repeating this processing will reconstruct a surface image two-dimensionally expressing the surface unevenness like that shown in FIGS. 5 and 9.

The apparatus repeats the procedure from step 52 to step 56 until the operator issues an end instruction (57). If the number of reconstructed straight lines exceeds the display area, it is possible to perform re-rendering upon returning to the upper end of the display area or update the latest image by scrolling/displaying.

Figure 10:
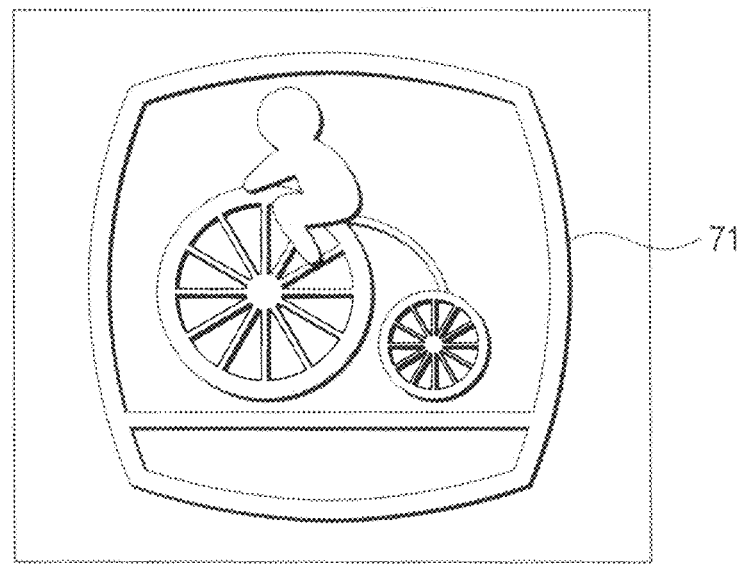
FIG. 10 is a view showing a target used in an experimental example in this embodiment.
Figure 11:
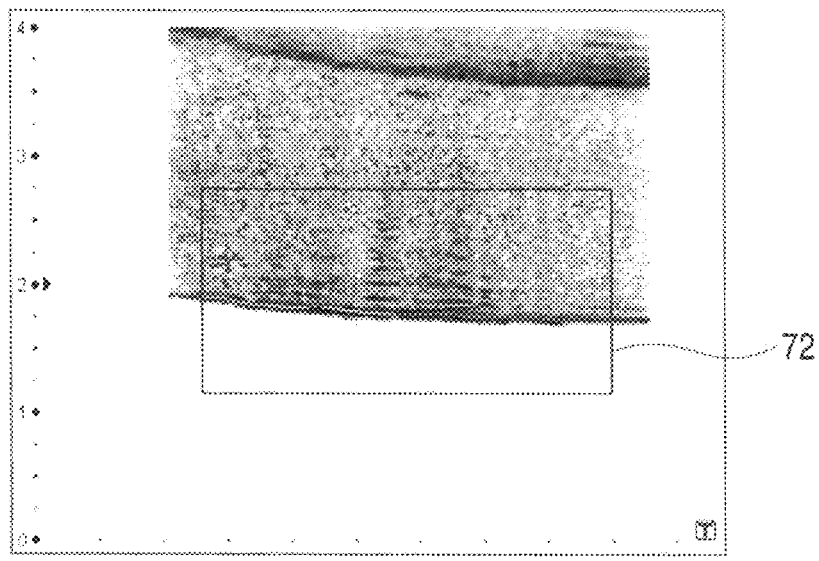
FIG. 11 is a view showing an actual tomogram of the target in FIG. 10.
Figure 12:
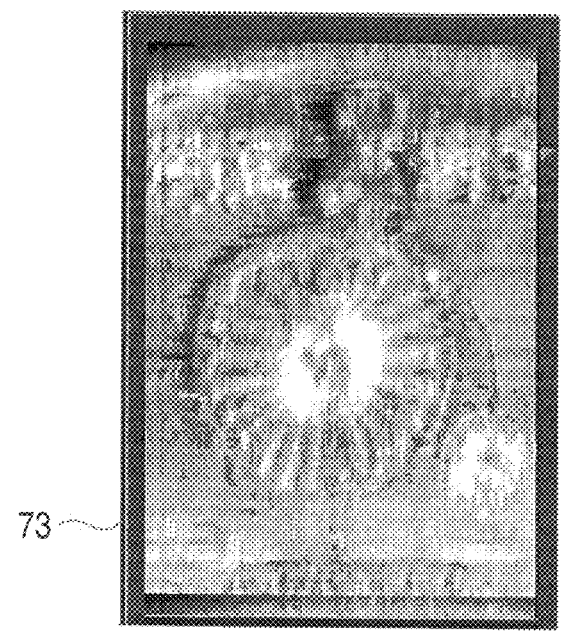
FIG. 12 is a view showing an actual surface image associated with the target in FIG. 10.

FIGS. 10 to 12 show an example of a basic experiment. An engraved medal 71 as an experimental sample made of a metal and having a width of about 4 cm was dipped in water. A 7-MHz band ultrasonic probe used in general diagnosis was slowly scanned on the surface of the medal. The unevenness of the engravings on the metal surface was 1 mm or less. Seeing a tomogram 72 during scanning indicates that a smoothed curve is obtained by the algorithm according to this embodiment, even though the boundaries on the metal surface are not necessarily linear. Seeing an image 73 obtained by reconstructing this curve indicates that the design of the medal is properly visualized.

<Application Using Mechanical Swinging Probe>

The above description is based on the assumption that the operator manually and three-dimensionally scans an object. It is also possible to perform such three-dimensional scanning by using a mechanical three-dimensional probe which mechanically swings or a two-dimensional matrix array probe whose delay directions can be electronically controlled.

In this case, the operator can obtain the above reconstructed image while keeping the probe itself at the same position. However, an arrangement for image processing and the like can be implemented by the same arrangement as described above.

<Display>

The reconstructed image in this embodiment is displayed on the display unit in parallel with a normal B-mode image or the like. Although an image in this embodiment can be independently displayed, the embodiment can display it in parallel with a B-mode image during scanning, thus providing suitable display.

According to this embodiment, when the operator simply scans, for example, the liver slowly and three-dimensionally, it is possible to visualize the state of a liver surface and allow easy diagnosis of the state of the unevenness of the liver surface. It is difficult to display such a diagnosis image by any conventional methods. That is, the present invention can provide new diagnosis information.

In addition, this technique need not acquire volume data necessary for a three-dimensional imaging method, and reduces the amount of data required for diagnosis. Alternatively, the technique need not perform computation such as volume rendering required for a general three-dimensional imaging method, and hence reduces the computation load on the CPU.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be without departing from the spirit of the inventions. The accompanying claims and their equivalents are intended to cover such forms or modifications as would fall within the scope and spirit of the inventions.

What is claimed is:

1. An ultrasonic diagnosis apparatus, comprising:
   an ultrasonic probe;
   ultrasonic transmission/reception circuitry configured to apply a driving pulse to the ultrasonic probe and generate echo signals associated with a plurality of scan lines;
   circuitry configured to
      generate image data based on the echo signals;
      extract a contour of an organ of an object from the image data;
      approximate the contour using a curve and determine a position of the curve in the image data; and
      generate a surface image expressing surface unevenness of the organ with brightness differences, the surface image being generated by arraying a plurality of brightness values of the curve in accordance with the position of the curve in the image data.

2. The apparatus according to claim 1, wherein the circuitry is further configured to generate the curve as a smoothed curve obtained by smoothing depth changes of the contour.

3. The apparatus according to claim 1, wherein the circuitry is further configured to generate the curve to pass between a train of depth local maximum points on the contour and a train of depth local minimum points on the contour.

4. The apparatus according to claim 1, wherein the circuitry is further configured to generate the curve to repeatedly cross the contour.

5. The apparatus according to claim 1, further comprising a display configured to display the surface image.

6. The apparatus according to claim 1, wherein the ultrasonic probe is one of a one-dimensional array type probe and a two-dimensional matrix array type probe configured to mechanically or electronically swing a scan plane.

7. The ultrasonic diagnosis apparatus of claim 1, wherein the circuitry is further configured to
   generate the image data, the image data being a plurality of tomograms;
   extract a plurality of contour lines, each contour line being associated with the organ and being generated from a corresponding tomogram of the plurality of tomograms;
   generate a plurality of curves, each curve being generated from a corresponding contour line of the plurality of extracted contour lines; and generate a plurality of one-dimensional brightness trains, each brightness train being a one-dimensional array of brightness values and being generated from brightness values along a corresponding curve of the plurality of curves, the surface image being generated by arraying the one-dimensional brightness trains in accordance with positions on corresponding scan planes.

8. An ultrasonic diagnosis apparatus, comprising:
an ultrasonic probe;
ultrasonic transmission/reception circuitry configured to apply a driving pulse to the ultrasonic probe and generate echo signals associated with a plurality of scan lines;
circuitry configured to
generate image data; and
generate an image by arranging a plurality of brightness values of a curve in accordance with a position of the curve in the image data, wherein the curve approximates a contour of an organ of an object.

9. The apparatus according to claim 8, wherein the circuitry is further configured to approximate the contour using the curve and determine the position of the curve in the image data.

10. The apparatus according to claim 8, wherein the circuitry is further configured to generate the image, which is an image expressing surface unevenness of the organ with brightness differences.

11. The apparatus according to claim 8, further comprising a display configured to display the image.

* * * * *